United States Patent [19]

Lersmacher et al.

[11] Patent Number: 4,547,069
[45] Date of Patent: Oct. 15, 1985

[54] TUBULAR CUVETTE FOR ATOMIC ABSORPTION SPECTROMETRY

[75] Inventors: Bernhard Lersmacher, Aachen, Fed. Rep. of Germany; Wilhelmus F. Knippenberg, Eindhoven, Netherlands

[73] Assignee: U.S. Philips Corporation, New York, N.Y.

[21] Appl. No.: 473,518

[22] Filed: Mar. 9, 1983

[30] Foreign Application Priority Data

Mar. 11, 1982 [DE] Fed. Rep. of Germany ....... 3208744

[51] Int. Cl.⁴ ...................... G01N 21/03; G01N 21/74
[52] U.S. Cl. ..................................... 356/244; 356/312
[58] Field of Search ................................ 356/312, 244

[56] References Cited

U.S. PATENT DOCUMENTS 3,817,629  6/1974  Witte ..................... 356/244

Primary Examiner—F. L. Evans
Attorney, Agent, or Firm—Paul R. Miller

[57] ABSTRACT

A cuvette having a thin-walled basic member of pyrolytic graphite is provided with annular graphite components in proximity to its ends. These parts are connected to form a unit which is further coated by an enveloping pyrolytic graphite coating. This cuvette having flanged parts is simpler to electrically contact and is mechanically stable.

9 Claims, 7 Drawing Figures

TUBULAR CUVETTE FOR ATOMIC ABSORPTION SPECTROMETRY

The invention relates to a tubular cuvette for atomic absorption spectrometry (AAS) having flange-shaped or flange-like parts, hereinafter referred to as "flanges" or "contact rings", which are provided at the ends of the tube or in the proximity thereof.

Such a tubular cuvette with electric current heating is known from DE-OS No. 22 21 184. In this known cuvette the electric current is applied to the tube ends substantially radially from without by the flange-shaped or flange-like parts which are constructed in particular in their thickness and thickness distribution so that so much thermal energy is generated in them and their thermal conductivity is so small that a cooling of the tube ends is sufficiently prevented. The flanges are either connected rigidly to the tube so that flanges and tube form one assembly, or flange and tube are mechanically separate components which contact each other at the tube ends at contact faces.

In a parallel Patent Application by the present Applicant a new type of cuvette is suggested see Ser. No. 473,380, filed Mar. 8, 1983. This new cuvette consists exclusively of pyrolytic graphite and is characterized by very small wall thicknesses, and hence, also has an extremely small "thermally-inert" mass.

The use of such thin-walled ($\delta \approx 100$ to $300$ $\mu$m) tubes involves certain problems as regards contacting to the current supplies of the AAS apparatus. The difficulty consists in that good (clamping) contacts, i.e. contacts which are uniform over the entire circumference of the cuvette tube, can be realized with reproducible contact resistances. Such an optimum reproducibility, however, is of considerable influence on the progress, and hence, on the result of a AAS analysis as well as for the handling of the cuvette in AAS apparatuses.

In very thin-walled cuvettes the contact itself, when contacting from the end face, is substantially a circular line. On the one hand this has certain advantages, since the heat dissipation from the cuvette in the, usually cooled, contact pieces of the apparatus can be kept very small and hence a very homogeneous temperature distribution over the length of the cuvette with very steep temperature gradients at the cuvette ends can be achieved. On the other hand, the above-mentioned difficulties of a reproducible contacting requires the cuvettes themselves to be worked with extreme precision and to be handled very carefully when inserted into the AAS apparatus.

It will be obvious that the above-described contacting problems can be reduced considerably when more solid contacts are used. This latter can be achieved in principle by two methods:

(a) by larger wall thickness of the tubes
(b) by using tubes having thickened ends in the form of toroidal or flange-like contacts.

Method (a) which in itself is usual in cuvettes of electrographite due to the necessarily larger wall thicknesses, may in principle also be used in pyrographite. However, thick-walled cuvettes of this material are very expensive (at least a factor 10 more expensive than the coated cuvettes presently obtainable in trade) and moreover the advantages of the "quick-action" and "low-mass" cuvettes suggested in the above-mentioned Patent Application Ser. No. 473,380, filed, Mar. 8, 1983, would be lost.

Method (b) is also used in practice already in cuvettes of "normal" graphite, for example, in the type of cuvette known from DE-OS No. 22 21 184. Although it is in principle possible to deposit cuvettes of pyrolytic graphite with flange-like ends immediately on suitably formed cores by deposition from the gaseous phase, such a method would also be very expensive since this requires—at least—very complicated multicomponent substrate bodies which after depositing a layer of pyrolytic graphite can be taken out of the envelope (mould releasable) and in addition requires expensive finishing measures.

It is the object of the invention to provide a technically perfect and economical solution of the above-described problems.

According to the invention this object is achieved in that the tube consists of pyrolytic graphite and that the tube and the flange-shaped or flange-like parts are provided with an envelope of pyrolytic graphite.

Further embodiments of the invention can be derived from the dependent claims.

The invention will now be described in greater detail with reference to the drawing and a few embodiments.

In the drawing

In the Figures a tube 1 is shown of pyrolytic graphite at the ends of which contact rings 2 of electrographite are provided. The assembly is covered with an envelope 3 of pyrolytic graphite.

Figure 1:
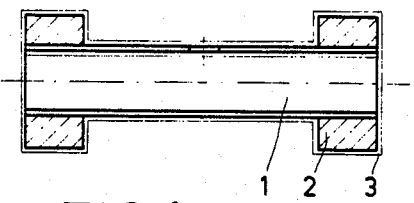
FIGS. 1 and 5 are longitudinal sectional views of a few tubular cuvettes.
Figure 2:
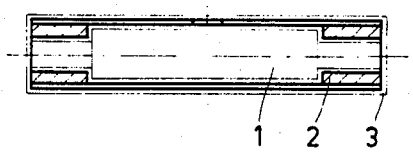
Figure 3:
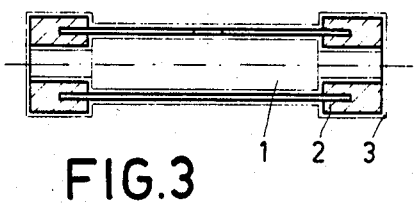
Figure 5:
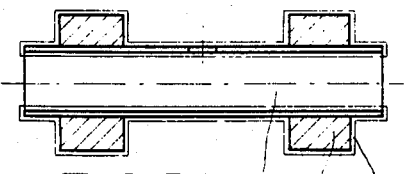

FIG. 1 shows a tubular cuvette with outer rings, FIG. 2 shows a tubular cuvette with inner rings and FIG. 3 shows a tubular cuvette with slip-on rings. In the tubular cuvette shown in FIG. 5 the rings are moved from the tube ends towards the tube centre. The different shapes and arrangements of the reinforcing rings and contact rings enable an optimum adaptation to the relevant contacting device of the AAS apparatus.

Figure 6A:
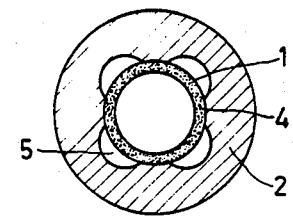
FIGS. 6a and 6b are side elevations of tubular cuvettes having specially shaped contact rings.
Figure 6B:
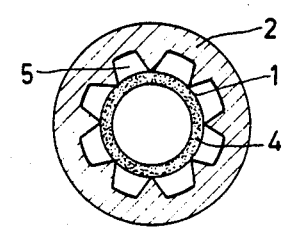
Figure 4:
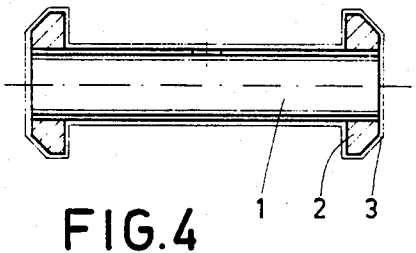

In manufacturing the cuvette according to the invention tubes of pyrolytic graphite are manufactured in a first step according to known methods and are further processed to thin-walled cuvettes according to the indications given in the above-mentioned Patent Application Ser. No. 473,380 filed Mar. 8, 1983. In a separate step (second step of the method) rings are manufactured, preferably from electrographite. Other materials are solid carbons, for example, vitreous carbon in a more solid and also in a more porous form, as well as (in exceptional cases) high-melting-point metals such as Mo, W, Ta and the like. The dimensions of the graphite rings must be matched to the dimensions of the cuvette tubes so that the two components can be combined according to the indications of FIG. 1 and that in such manner that a certain clamping fit is ensured so that no special additional measures for fixing are necessary. It has been found that this can very readily be done as a result of the good processibility of the two materials (graphite, pyrographite). FIGS. 6a and 6b show that the reinforcement and contacting layer can be extremely modified as regards their profile and shape, respectively. For example, they may be shaped so that they contact the basic tube 1 only a in few points 4 in a punctiform or area-like manner. Such contacts interrupted by ruptures 5 enable within certain limits an influencing of the current and heat flow and hence a homogenization of the temperature profile over the length of the cuvette in the sense of a steeper temperature gradient at the cuvette ends. After assembling the individual components, at least one further coating with pyrolytic graphite is carried out (third step of the method). The resulting layer enveloping on all sides connects the parts to a member, namely to a cuvette having fixed contacting flanges and moreover has the effect of a sealing of the whole surface. The surface sealing on all sides automatically associated with the second coating corresponds to the concept of an endeavoured passivation of the processed cuvette explained in DE-OS No. 29 49 275. This passivating effect generally produces an increase of the life. As described in the above-mentioned Patent Application Ser. No. 473,380, filed Mar. 8, 1983, however, the case of an activated cuvette surface is also often desirable (by processing). It is always a question of the required minimum life (number of heatings) or of the increased reactivity whether the second layer is to be removed in particular on the inside of the cuvette by grinding away. In this case a new type of flange cuvette is obtained with activated inner and passivated outer surface. The cuvette manufactured in this manner can also be referred to and characterized, respectively, as a compound cuvette.

EXAMPLE

In a known method, pyrographite layers were deposited from a hydrocarbon-containing gas on cylindrical solid rods of electrographite having a diameter of 4.9 mm. After cooling and taking out of the CVD reactor the substrate rods and the envelopes could be separated from each other. The latter had the shape of thin-walled tubes, inside diameter 5 mm and outside diameter approximately 5.5 mm, so a wall thickness of approximately 250 $\mu$m. These tubes were processed to cuvettes of 28 mm length and 5.4 mm outside diameter, so 200 $\mu$m wall thickness, by means of cutting, grinding and drilling. In a separate step, rings of very pure electrographite of 5.4(+0.01 to 0.02) mm inside diameter, 1.5 mm width and 1.0 mm thickness were manufactured. These rings could be slid on the ends of the cuvettes in a tight-fitting manner. The interconnection of the parts was carried out in a second coating step. It has been found that a 10 $\mu$m thick enveloping and connecting layer of pyrolytic graphite is sufficient both electrically and mechanically for cuvettes of the above-mentioned dimensions. The overall electric resistance measured over the length was approximately 0.1 ohm.

In addition to their electric function, the contact rings produce a further effect: the very thin-walled cuvette tubes often warp as a result of inner stresses which build up in the anisotropic pyrolytic graphite upon cooling. The tubes become non-circular and may even burst or tear. These deformations are suppressed by providing the contact rings and the cuvette is mechanically stabilized. The major and essential effect is, however, that the contact rings ensure a homogeneous supply of the heating current and hence a homogeneous temperature distribution about the circumference and hence also over the length of the cuvette tube.

The removal of parts of the outer pyrolytic graphite layers so that the envelope, for example, on the surfaces contacting the apparatus contacts, shows interruptions, presents a possibility of modifying the contact resistances and the heat flow in certain limits.

The subsequent removal of the second layer on the inner wall of the cuvette (for example, by grinding) selectively removes again the passivation produced by the secondary coating and hence increases the reduction potential in particular in the range in which the analysis sample is provided.

Summarizing it is to be noted that the cuvette according to the invention has a thin-walled basic member of pyrolytic graphite which is provided at its ends with annular graphite parts. These parts are connected to form a unit by means of an enveloping pyrographite layer. The flanged cuvette thus manufactured is simpler to contact and mechanically stabilized. The advantages of a "low-mass, quick-action" cuvette are maintained as much as possble in this type of cuvette also. The manufacture of the cuvette is technically simple and favourable as regards cost.

What is claimed is:

1. In a tubular cuvette for atomic absorption spectrometry comprising a tubular member having inner and outer walls and having flange-like parts disposed at least in proximity to ends of said tubular member, the improvement comprising said tubular member consisting of pyrolytic graphite, and said tubular member and flange-like parts being provided with a common envelope of pyrolytic graphite.

2. A tubular cuvette according to claim 1, wherein said tubular member has a wall thickness from 50 microns to 1000 microns.

3. A tubular cuvette according to claim 2, wherein said wall thickness is 100 microns to 300 microns.

4. A tubular cuvette according to claim 1, wherein said flange-like parts consist one of electrographite, vitreous carbon, or high-melting point metals.

5. A tubular cuvette according to claim 1, wherein said flange-like parts engage said tubular member at only a few areas.

6. A tubular cuvette according to claim 1, wherein said common envelope is from 1 micron to 100 microns in thickness.

7. A tubular cuvette according to claim 6, wherein said thickness is 10 microns.

8. A tubular cuvette according to claim 1, wherein said common envelope has interruptions.

9. A tubular cuvette according to claim 1, wherein said inner walls are free of said common envelope of pyrolytic graphite.

* * * * *